United States Patent
Starling et al.

(10) Patent No.: US 6,358,532 B2
(45) Date of Patent: Mar. 19, 2002

(54) CALCIUM PHOSPHATE MICROCARRIERS AND MICROSPHERES

(75) Inventors: L. Brian Starling, Golden; James E. Stephan, Arvada, both of CO (US)

(73) Assignee: CaP Biotechnology, Inc., Golden, CO (US)

(*) Notice: Subject to any disclaimer, the term of this patent is extended or adjusted under 35 U.S.C. 154(b) by 0 days.

(21) Appl. No.: 09/788,103

(22) Filed: Feb. 15, 2001

Related U.S. Application Data

(63) Continuation of application No. 09/402,308, filed on Oct. 1, 1999.

(51) Int. Cl.[7] .............................. A61K 9/14; A61K 9/16; A61F 13/00
(52) U.S. Cl. ........................ 424/489; 424/426; 424/422; 424/423; 424/602; 424/490
(58) Field of Search ............................ 424/489, 426, 424/423, 602, 490, 422; 423/308; 523/113, 115; 623/8, 23.72

(56) References Cited

U.S. PATENT DOCUMENTS

| | | | |
|---|---|---|---|
| 3,875,273 A | 4/1975 | Martin | 264/43 |
| 4,448,884 A | 5/1984 | Henderson | 435/241 |
| 4,564,532 A | 1/1986 | Henderson | 427/2 |
| 4,661,407 A | 4/1987 | Henderson | 428/403 |
| 4,757,017 A | 7/1988 | Cheung | 435/204.23 |
| 4,798,585 A * | 1/1989 | Inoue et al. | 604/93 |
| 4,987,068 A | 1/1991 | Trösch et al. | 435/41 |
| 5,045,201 A | 9/1991 | Dubois | 210/502 |
| 5,047,031 A | 9/1991 | Constantz | 606/77 |
| 5,171,326 A | 12/1992 | Ducheyne et al. | 623/66 |
| 5,192,324 A | 3/1993 | Kenna | 623/16 |
| 5,225,123 A | 7/1993 | Torobin | 264/43 |
| 5,262,320 A | 11/1993 | Stephanopoulos et al. | 435/240.23 |
| 5,324,519 A * | 6/1994 | Dunn et al. | 424/426 |
| 5,397,759 A | 3/1995 | Torobin | 502/415 |
| 5,422,340 A | 6/1995 | Ammann et al. | 514/12 |
| 5,480,827 A | 1/1996 | Guillemin et al. | 435/240.23 |
| 5,492,822 A | 2/1996 | Lange, III et al. | 435/196 |
| 5,510,262 A | 4/1996 | Stephanopoulos et al. | 435/240.23 |
| 5,525,148 A | 6/1996 | Chow et al. | 106/35 |
| 5,538,887 A | 7/1996 | Peindhl et al. | 435/240.243 |
| 5,922,025 A * | 7/1999 | Hubbard | 424/423 |

FOREIGN PATENT DOCUMENTS

WO  00/46147  8/2000

OTHER PUBLICATIONS

Looby et al., *Trends in Biotechnology*, 8:204–209, 1990.
Park et al., *Biotechnology Bioengineering*, 41:25–34 1993.
Lee et al., Production of Biologicals from Animal Cells in Culture, R.E. Butterworth–Heinemann et al., eds. pp. 400–405, 1991.
Matsushita et al., "High Density Culture of Anchorage Animal Cells by Polyurethane Foam Packed Bed Culture Systems," *Applied Microbiology Biotechnology*, 35:159–64, 1991.
J.M. Davis (ed.) *Basic Cell Culture*, (Cartwright and Shah), p. 78, Oxford University Press, New York 1994.
A. Tampieri, *J. Mat. Sci.: Matls in Med.*, vol. 8, pp. 29–37, 1997.
D. Wilcox, "Hollow and Solid Spheres and Microspheres: Science and Technology Associated With Their Fabrication and Application," Materials Research Society Symposium Proceedings, vol. 372, 1995 (contents).
Bio–Rad Bulletin No. 1115.
Hideki Aoki, In *Medical Applications of Hydroxyapatite* (contents).
Sundaram et al., *J. of Liq. Chromatog.* 18(5), 925–939 (1995).

* cited by examiner

*Primary Examiner*—James M. Spear
*Assistant Examiner*—Blessing Fubara
(74) *Attorney, Agent, or Firm*—Sheridan Ross P.C.

(57) ABSTRACT

The present invention provides calcium phosphate-based (CaP) microcarriers and their use, for example, in cell culturing systems, chromatography, and implantable biomedical materials.

32 Claims, 2 Drawing Sheets

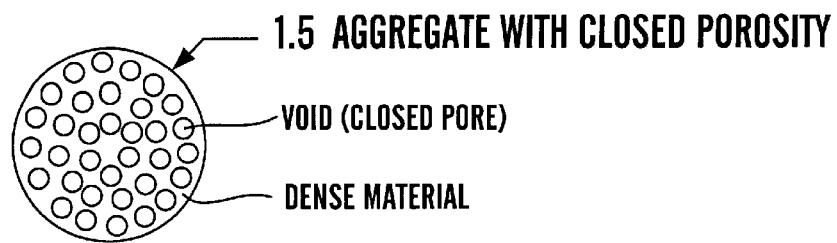
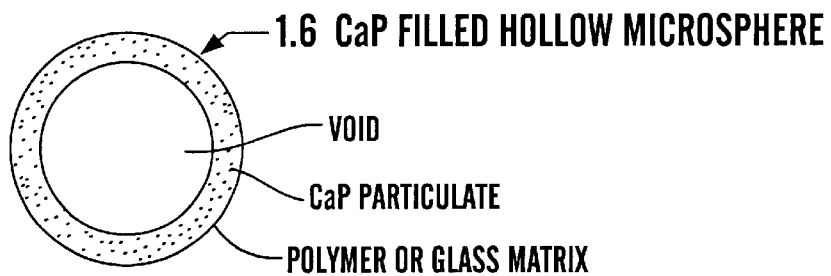
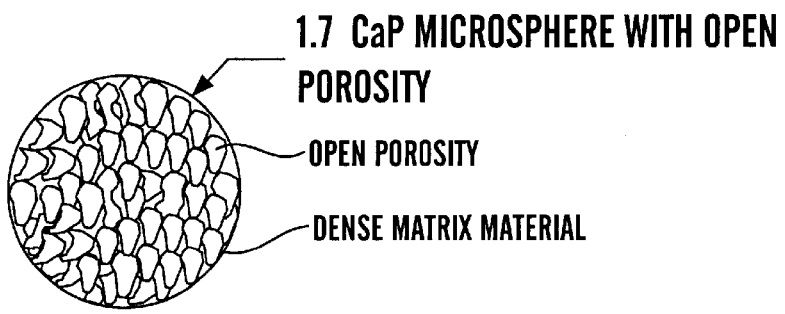
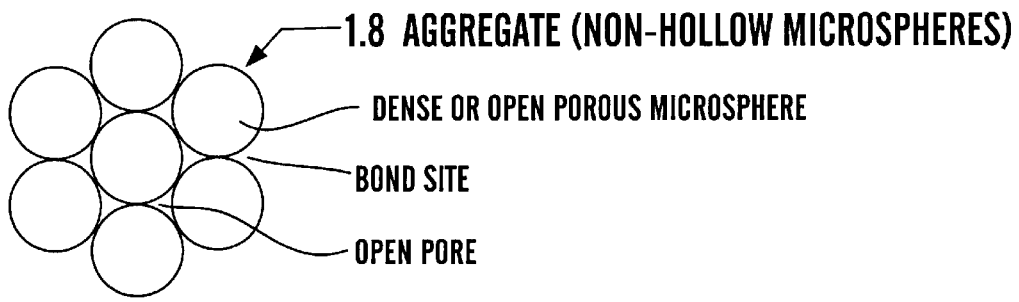
*FIG. 1-2*

CALCIUM PHOSPHATE MICROCARRIERS AND MICROSPHERES

CROSS REFERENCE TO RELATED APPLICATION

The present application is a continuation of U.S. patent application Ser. No. 09/402,308, filed Oct. 1, 1999, entitled "CALCIUM PHOSPHATE MICROCARRIERS AND MICROSPHERES", which is incorporated herein by this reference.

FIELD OF THE INVENTION

The Invention disclosed herein relates to calcium phosphate (CaP) microcarriers and microspheres and their use, for example, in cell culturing systems, chromatography analysis and processing, and implantable materials useful for biomedical implants.

BACKGROUND

Revolutionary advances in biotechnology and genetic engineering have created enormous potential for marketing cellular by-products, including for example, proteins, including protein pharmaceuticals such as interferon, monoclonal antibodies, TPA (Tissue Plasminogen Activator), growth factors, insulin, and cells for transplantation. The demand for these products has grown tremendously and will continue to do so, creating a need for efficient methods of producing industrial quantities of cell-derived pharmaceuticals and other products. Further, the demand for efficient methods of analyzing and isolating biological products through chromatographic technology, and the need to improve bio-implantables continues to grow.

Research and study of cell structure and morphology are fundamental to continued progress in the diagnosis and treatment of human diseases. Numerous cell products are of vital importance therapeutically and commercially, including, for example, hormones, enzymes, viral products, vaccines, and nucleic acids. The production of these products requires large scale cell culture systems for their production.

Mammalian cells can be grown and maintained in vitro, but are generally anchorage-dependent, i.e., they require a solid surface or substrate for growth. The solid substrate is covered by or immersed in a nutrient medium particular to the cell type to be cultured. The nutrient medium and solid substrates are contained in a vessel and provided with an adequate supply of oxygen and carbon dioxide to support cell growth and maintenance. Cell cultures may be batch systems, in which nutrients are not replenished during cultivation although oxygen is added as required; fed batch systems, in which nutrient and oxygen are monitored and replenished as necessary; and perfusion systems, in which nutrient and waste products are monitored and controlled (Lubiniecki, *Large Scale Mammalian Cell Culture Technology*, Marcel Dekker, Inc., New York, 1990).

The primary commercial systems used for mammalian cell culture use solid matrix perfusion and microcarrier bead systems (Lubineicke, supra). The solid matrix perfusion systems utilize glass columns packed with glass beads or helices, which form a matrix as the solid substrate for cell growth. Once cells have attached to the matrix, medium is continuously recycled from a storage vessel for support of cell growth and maintenance. A similar perfusion system uses hollow fibers as the solid matrix instead of beads.

In microcarrier systems, small spheres are fabricated, for example, from an ion exchange gel, dextran, polystyrene, polyacrylamide, or collagen-based material. These materials have been selected for compatibility with cells, durability to agitation and specific gravities that will maintain suspension of the microcarriers in growth mediums. Microcarriers are generally kept in suspension in a growth medium by gently stirring them in a vessel. Microcarrier systems are currently regarded as the most suitable systems for large-scale cell culture because they have the highest surface to volume ratio and enable better monitoring and control. Nevertheless, current microcarrier culture systems have a number of serious disadvantages: small microcarrier cultures cannot be used to inoculate larger microcarrier cultures; therefore, a production facility must use other culture systems for this purpose; the cost of microcarriers is high, which can necessitate reprocessing of the microcarriers for reuse with the attendant costs; and the oxygen transfer characteristics of existing microcarrier systems are rather poor.

Specific forms of calcium phosphate ceramic have been identified for use in microcarriers to support anchorage-dependent cells in suspension. These specialized ceramics provide a material which is biomimetic, i.e., it is composed of mineral species found in mammalian tissues, and which can be further applied to a variety of in vitro biological applications of commercial interest. A number of common cell lines used in industrial applications require attachment in order to propagate and need substrate materials such as microcarriers for large scale cultivation. U.S. Pat. No. 4,757,017 (Herman Cheung) teaches the use of solid substrates of mitogenic calcium compounds, such as hydroxylapatite (HA) and tricalcium phosphate (TCP) for use in in vitro cell culture systems for anchorage-dependent mammalian cells. The unique features of this technology include the growth of cells in layers many cells thick, growth of cells that maintain their phenotype and the ability to culture cells for extended periods of time. Cheung demonstrated the application of this technology for culturing red blood cells. A current limitation of this technology is that the microcarriers are only available in a non-suspendable granular form. The density of these microcarriers further limits the ability to scale-up this technology for large bioreactors, which require a suspendable microbead carrier.

A complementary system using an aragonite ($CaCO_3$) is disclosed in U.S. Pat. No. 5,480,827 (G. Guillemin et al). Although this patent also teaches the importance of calcium in a support system for mammalian cell culture, the calcium compound was not in a suspendable form.

The concept of fabricating a suspendable microcarrier bead with a minor component of glass was discussed by A. Lubiniecki in *Large-Scale Mammalian Cell Culture Technology* in which a minimal glass coating was applied to a polymer bead substrate by a chemical vapor deposition process or low temperature process. This approach also was disclosed in U.S. Pat. No. 4,448,884 by T. Henderson (see also U.S. Pat. Nos. 4,564,532 and 4,661,407). However, this approach primarily used the polymer bead substrate to maintain suspendability.

An example of the use of non-suspendable or porous ceramic particles for cell culture is taught by U.S. Pat. No. 5,262,320 (G. Stephanopoulos) which describes a packed bed of ceramic particles around and through which oxygen and growth media are circulated to encourage growth of cells. U.S. Pat. No. 4,987,068 (W. Trosch et al.) also teaches the use of porous inorganic (glass) spheres in fixed bed or fluidized bed bioreactors. The pores of the particles act as sites for the culture of cells. Conversely, Richard Peindhl, in U.S. Pat. No. 5,538,887, describes a smooth surface cell culture apparatus which would limit cell attachment to chemical adhesion and prevent mechanical interlocking.

Macroporous glass beads also have been reported by D. Looby and J. Griffiths, "Imobilization of Cells In Porous Carrier Culture", *Trends in Biotechnology*, 8: 204–209, 1990, and magnesium aluminate porous systems by Park and Stephanopolous, "Packed Bed Reactor With Porous Ceramic Beads for Animal Cell Culture, *Biotechnology Bioenginering*, 41: 25–34, 1993. Fused alumina fs have been reported by Lee et al, "High Intensity Growth of Adherent Cells On a Porous Ceramic Matrix. *Production of Biologicals from Animal Cells in Culture, editors*, R. E. et al, Butterworth-Heinemann pp. 400–405, 1991, and polyurethane foam by Matsushita et al, "High Density Culture of Anchorage Dependent Animal Cells by Polyurethane Foam Packed Bed Culture Systems", *Applied Microbiology Biotechnology*, 35: 159–64, 1991.

Fluidized bed reactors have been used for cell culture as reported by J. M. Davis (editor), *Basic Cell Culture*, (Cartwright and Shah), Oxford University Press, New York, 1994, but require carrier systems with densities between 1.3 and 1.6 g/cc. According to Cartwright (J. M. Davis, supra.), generally, in fluidized beds, cells do not grow on the exterior surface of carriers where they would be dislodged by inter-particle abrasion. Instead, as with macroporous microcarriers, they colonize the interior pores where they proliferate in a protected microenvironment. As examples, (Cartwright, supra, p. 78) cell carriers used in fluidized beds include glass beads (Siran by Schott Glass), and collagen microspheres produced by Verax. Cartwright also disclosed other conventional microcarriers weighted with $TiO_2$ (Percell Biolytica products) and IAM-carrier polyethylene beads weighted with silica.

SUMMARY OF INVENTION

Examples of the microcarriers of the present invention are set forth in FIG. 1.

The present invention provides hollow microbeads having a density of about 1.01 grams/cc to about 1.12 grams/cc. More specifically, the hollow microbeads comprise 0 to 100% hydroxylapatite (HA), 0 to 100% tricalcium phosphate (TCP) and/or 0 to 100% other calcium phosphate compounds. The hollow microbeads comprise a wall, wherein the wall may be impermeable to aqueous media. The essentially spherical hollow microbeads can have a diameter of from about 100 micrometers to about 6 millimeters. In another embodiment, the hollow microbead can further comprise a porous coating and/or a biological coating.

The present invention also provides hollow microbeads having a density from about 1.2 grams/cc to 2.0 grams/cc. These hollow microbeads can further comprise a porous coating and/or a biological coating.

Also provided are biomedical implants comprising the above-described microbeads. The biomedical implants can further comprise a biological material or pharmaceutical agent. More specifically, the biomedical implants have a density from about 25% to about 75% of the material's theoretical density. (By "theoretical density" is meant the density of a microbead having no pores.) The biomedical implant may comprise a microbead wherein the microbead comprises a wall that is essentially impermeable or porous to aqueous media. The biomedical implant may also comprise microbeads comprising holes, i.e., portals or channels.

Also provided are chromatographic columns comprising the hollow microbeads as set forth above.

Also provided are aggregates comprising the hollow microbeads as set forth above. Such aggregates can be used as biomedical implants and chromatographic columns. The aggregates may be bonded by cementations agents.

The invention further provides hollow and solid glass or polymer microbeads formed with or coated with particulate HA, TCP and other CaPs.

Also provided are hollow and solid microbeads comprising composites of HA, TCP, other CaPs and ceramic, including glass and polymeric materials. These microbeads may have abraded surfaces and aggregates may be made from them. The aggregates may be used in biomedical implants and in chromatographic columns.

Also provided are suspendable and non-suspendable aggregates comprising closed and/or open pores, foamed structures of ceramic, including glass, and/or polymeric composite materials. These aggregates can comprise HA, TCP and other CaP coatings, porous coatings, or biological coatings including growth factors. Biomedical implants can be made comprising these aggregates. Also provided are methods of augmenting tissue comprising implanting these biomedical implants. The biomedical implants may further comprise a biologically active agent and have a density from about 25% to about 75% of the material's theoretical density. Chromatographic columns also can be made from such aggregates.

DETAILED DESCRIPTION OF THE INVENTION

Figure 1:
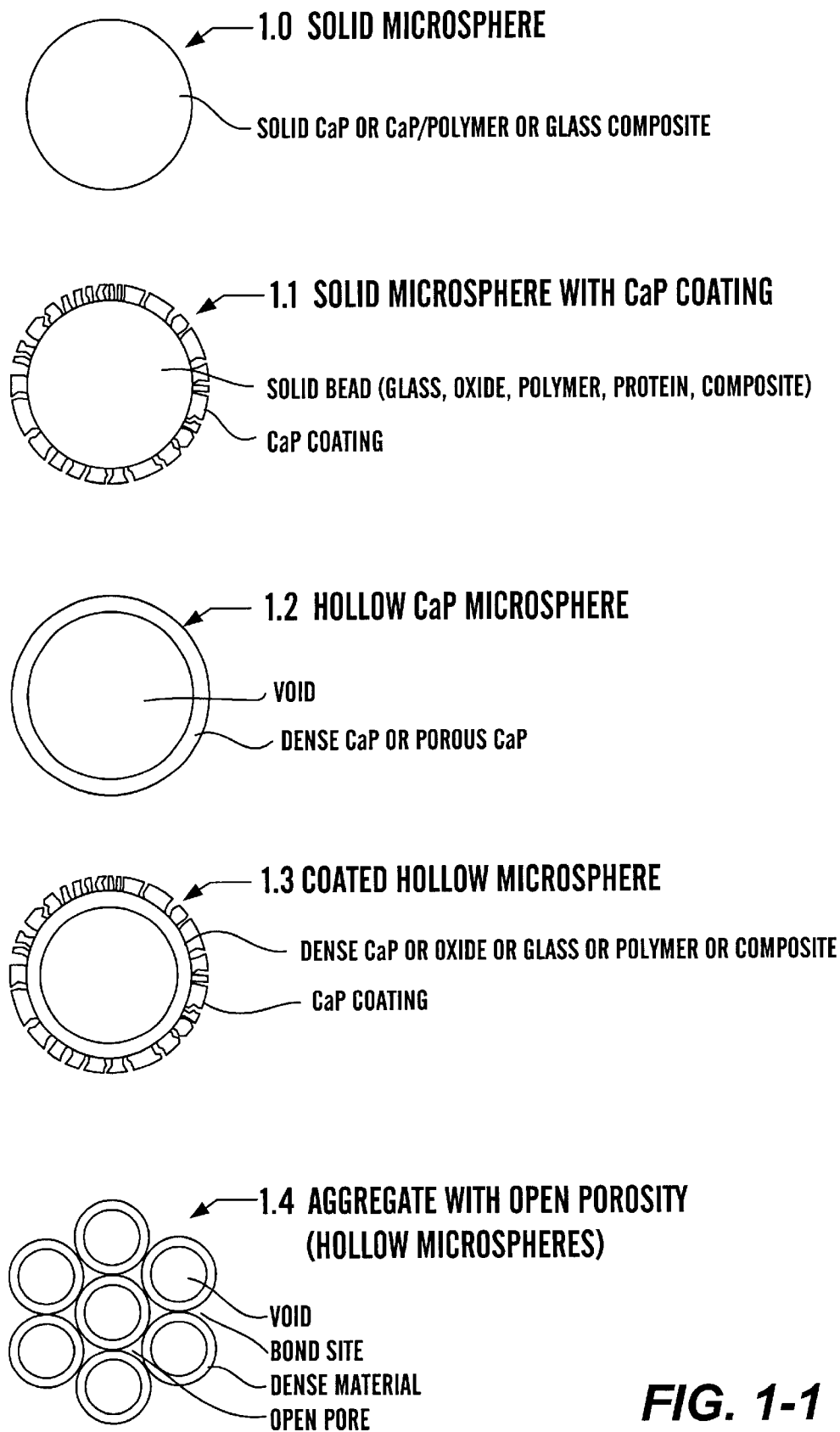
FIG. 1 shows examples of microcarriers (microbeads) of the present invention.

CaP Microbead Processing Method for Producing a Suspendable Microcarrier Substrate The present invention relates to suspendable microbeads (also referred to herein as microcarriers and microspheres). These microcarriers (FIG. 1) can be used for mammalian cell culturing applications requiring anchorage-dependent cells in laboratory and commercial bioreactors. The microspheres may be produced by specialized slurry processing and subsequent use of a coaxial blowing nozzle, to create the enclosed porosity structure of the microspheres for suspension in aqueous-based cell culturing media. More specifically, the CaP microsphere is hollow and comprised of suitable mixtures of 0 to 100% HA, and 0 to 100% TCP, and/or other calcium phosphate compounds including any mixture thereof. The preferred process for the CaP microcarrier ceramic slurry process uses a nozzle-reactor system with slurry droplet blowing agent, to produce hollow microspheres in a size range of about 0.5 millimeter to about 6 millimeter diameter and specific wall thicknesses that sinter to an aqueous impermeable state sufficient to maintain suspendability in culture medium. As examples, the microcarrier wall thicknesses are about 20 to about 40 micrometers for 0.5 mm diameter, about 50 to about 80 micrometers for 1.0 mm diameter, and about 170 to about 230 micrometers for 3.0 mm diameter microcarriers to maintain suspendability. More specifically, the density of the microspheres is preferably in the range from about 1.01 gms/cc to about 1.12 gms/cc. Preferably, the density range is controlled from about 1.01 gms/cc to about 1.06 gms/cc. Final hollow microsphere dimensions are adjusted to compensate for shrinkage normally encountered during sintering from the formed state, which in the case of CaP mixtures of HA and TCP is typically in the range of about 15–25% linear shrinkage.

Furthermore, using variations in processing conditions or in post-microsphere fabrication processing, the hollow microspheres can have either rough (e.g., textured or abraded) or smooth surfaces for tailoring the surface condition to either enhance the attachment of cells for increasing the production of cell by-products, or to enhance the release of grown cells in culture for applications requiring the proliferation of cells. The surfaces of the hollow microspheres may also comprise other substances, including, for example, biological coatings, including growth factors, selected proteins, amino acids, collagen, and other such materials.

Additionally, the density of the hollow microsphere can be adjusted to about 1.2 gms/cc to about 2.0 gms/cc for fluidized or fixed bed applications. The microsphere wall thickness may be increased for any given suspendable size to achieve this range. Also, for fixed bed applications, the density of the microcarrier may be greater than 1.6 gms/cc.

Alternate Method for Fabricating Hollow CaP Microcarriers with Diameters Less than 500 Micrometers (Sol Gel Type System)

In this aspect of the invention, a reaction precipitation method for producing submicron CaP microspheres (FIGS. 1, 1.2) is used in conjunction with an oleyl alcohol condensing solution to fabricate hollow microspheres. The CaP precipitated solution is nozzle-sprayed onto the oleyl alcohol using nozzle size, pressure, and spray distance to control the size of the microsphere. This method utilizes a low solids to liquid ratio (typically less than about 20%) in conjunction with hot oleyl alcohol for concentrating the CaP solids into a shell for forming the microspheres. After the fabricating step, the microspheres are dried, sintered and classified to size and density by traditional sieving and air classification methods. The microspheres also may be classified to desired densities for buoyancy by liquid density separation methods. The degree of sintering also is used to control the porosity or permeability of the microsphere. Therefore, a suspendable or non-suspendable (porous/non-porous) microcarrier may be produced by this method. More specifically, for fixed bed or fluidized bed reactors, higher density microcarriers are produced to meet the requirements for these non-suspendable applications.

Alternate Method for Fabricating Hollow CaP Microspheres by Coating on Wax or Other Organic Microbeads (FIGS. 1, 1.2)

Slurries or powders of calcium phosphate compounds are applied to the surfaces of wax or other organic microbeads. The organic microbead is removed by thermal decomposition, solvent extraction, or a combination thereof. The slurries or powders may incorporate binder to increase the strength of the shell formed on the wax or organic microbead, and may further aid in maintaining the formed CaP microsphere during removal of the wax or organic substrate. If required, the slurry solids content can be adjusted to increase or decrease the density of the CaP microsphere. Likewise, powder can be compacted around the wax or organic microbead to increase the density of the resulting CaP microsphere. After the fabrication step, the microspheres are dried, sintered and classified to size and density by traditional sieving and air classification methods. The microspheres also may be classified to desired densities for buoyancy by liquid density separation methods. The degree of sintering also is used to control the porosity or permeability of the microsphere. Therefore, a suspendable or non-suspendable (porous/non-porous) microcarrier may be produced by this method. More specifically, for fixed bed or fluidized bed reactors, higher density microcarriers are produced to meet the requirements for these non-suspendable applications.

Porous CaP Coatings for Bonding to the Substrate Surfaces of Hollow or Solid Beads or Microbeads Comprised of CaP, Glass, Other Oxide Ceramics or Polymers. Proteinaceous Materials or Composite Materials (FIGS. 1, 1.1 and 1.3)

A further object of this invention relates to porous CaP coatings that are comprised of suitable mixtures of particulate HA, TCP and/or other calcium phosphate compounds, and varying amounts of porosity for cell culturing applications. The benefits of CaP coatings include enhanced cell attachment, the protection of cells during culturing, and increased surface area for cell proliferation on a variety of substrates, including dense CaP and other dense or porous substrate materials. The purpose of CaP coatings on non-CaP substrates is to enhance the beneficial bioactivity of the substrate surface in cell culturing applications.

More specifically, two size ranges of porosity have been identified which include pore sizes less than about 30 micrometers for increased chemical activity of the substrate, and about 30–80 micrometers for in-growth by cells, protection of cells and enhanced chemical activity of the substrate. For either pore size range, the amount of porosity is typically greater than about 10% but less than about 60% to ensure mechanical integrity of the coating. More specifically, the amount of porosity to ensure interconnectivity should be greater than about 20%. Appropriate methods for applying CaP coatings include a slurry coating technique and/or applying adherent powder/particulates. The coatings may comprise open and/or closed porosity. Specific "pore formers" which produce the desired pore size range include various organic materials, which are varied in amount to produce porous CaP coatings for use in cell culturing applications. During the thermal processing cycle for sintering, the pore formers decompose leaving channels of interconnected porosity for pore volumes typically greater than about 20%.

Microbead substrate materials to be coated include, for example, dense CaP, and other oxide ceramics such as alumina, mullite, porcelain or glass. These substrate materials may be used to produce hollow or solid microspheres for cell culturing applications. The CaP coatings are applied to either unsintered or pre-sintered microspheres, and subsequently re-sintered for bonding. The substrate also may be re-heated to soften the surface in the case of a glass substrate. The CaP coating can be applied to porous substrates and then co-sintered to enhance bonding and further density the substrate layer. For polymeric and proteinaceous substrates, the preferred method for bonding is reheating the substrate material to soften the surface or applying a secondary bio-adhesive material to provide a bonding layer.

Aggregate Suspendable Microcarriers with Open Porosit (FIGS. 1, 1.4)

CaP microcarrier spheres are prepared as described above using a nozzle method from either a modified sol gel process or powder slurry process. The preferred embodiment of this aspect of the invention requires hollow microspheres with densities less than 1 gm/cc which are subsequently bonded with CaP—prepared powder slurry, calcium phosphate/sulfate cements, or sol gel-modified slurries in the unfired state for producing aggregates. Lower initial microsphere densities are required to offset the additional weight of the bonding slurries for achieving final suspendability in the range of about 1.00 gms/cc to about 1.12 gms/cc. After sintering, aggregates are sized by well known ceramic granulating/grinding and sieving methods. The sized aggregates are then sorted for density by liquid density separation methods. Liquid densities are prepared in the desired range for buoyancy and aggregates are separated based on the suspending properties. The starting sphere size can be used to control the open pore size and pore size distribution. One advantage of this method is that the open pores are used as sites for cell attachment and growth, thereby providing protection to the cultured cells and additional surface area for enhancing growth of cells. As stated above, the aggregate density is increased by addition of bonding slurry and/or additionally increasing the wall thickness of starting microspheres for use in fixed bed or fluidized bed reactors as examples of non-suspendable applications.

Aggregate Suspendable Microcarriers with Closed Porosity (FIGS. 1, 1.5)

As an alternative to a large, single void hollow microsphere, the closed porosity of the microcarrier can be distributed in multiple, isolated pores to reduce the density of the CaP in meeting the suspendability requirement. Closed porosity refers to microcarriers wherein voids are separated by dense material not open to the external surface. The preferred approach for creating closed porosity within the aggregate consists of the use of a closed-cell organic pore former material which produces about 60% to 70% closed porosity within the aggregate. After sintering, aggregates are sized by well known ceramic granulating/grinding and sieving methods. The sized aggregates may then be sorted for density by liquid density separation methods. Liquid densities may be prepared in the desired range for suspendability and aggregates are separated based on the suspending property. As stated above, the aggregate density is increased for use in fixed bed or fluidized bed reactors.

Composite Suspendable or Non-Suspendable Microcarriers (FIGS. 1, 1.0 and 1.6)

The preferred embodiment of this aspect of the invention relates to the incorporation of substantial volume fraction of CaP powder or particulate filler in a hollow or solid natural or synthetic polymer (e.g., polyethylene, polystyrene, dextran, gelatin) and/or glass microsphere. More specifically, the void volume in the hollow microsphere structure of a polymer or glass reduces the bulk density. As a result, the microcarrier can accommodate a higher CaP filler solids content and still meet the suspendability requirement. These microcarriers employ a variety of hollow glass or polymer microsphere processing methods. Subsequently, a CaP filler is incorporated to increase density to the desired suspendability.

As an alternative to the hollow polymer or glass microsphere, substantial amounts of "closed porosity" in the polymer or glass also allows for higher CaP filler additions due to the lower initial bulk density of the polymer or glass component in the composite. The closed porosity in the polymer or glass can be created, for example, by a foaming agent or control of sintering parameters to produce closed porosity. After the composite microsphere having a size of about 100 3to about 500 micrometers is made, the surface can be modified by abrading to increase exposure of the CaP filler for enhanced cell attachment and growth activity. The density of the microcarrier composite also can be increased using higher levels of CaP filler in either a hollow microsphere or solid form for fixed bed or fluidized bed reactor applications. Additionally, non-suspendable or suspendable microcarriers may be fabricated from monolithic (continuous solid) forms of combined CaP filler and polymer and/or glass materials (without or with porosity) which are subsequently granulated, ground or chopped into desired sizes and shapes.

CaP Non-Suspendable Microcarrier with Open Porosity (FIGS. 1, 1.2, 1.7 and 1.8)

CaP non-suspendable microcarrier spheres with open porosity are prepared as described above using a conventional spray drying method or pelletizing method well known in the art from either a modified sol gel process or powder slurry process. Also the method taught by Martin (U.S. Pat. No. 3,875,273, supra.) can be used to form open porous microcarriers. The preferred shape of the individual microcarrier produced by the methods described above is sphere-like with a continuous porous phase (FIGS. 1, 1.8). An alternative shape of microcarrier is a hollow microsphere having a continuous porous wall that connects the central microsphere void to the outer surface (FIGS. 1, 1.2). This form of microcarrier can be produced by the reactor nozzle method taught by Torobin (U.S. Pat. No. 5,397,759). The open porosity of microspheres is created by sintering at a lower temperature of about 1100° C., which is less than that typically required to densify the material, or by adding a pore former as previously discussed, followed by sintering. The preferred embodiment of this invention requires microspheres with densities greater than 1.12 gm/cc for packed or fluidized bed bioreactors.

The above-described microspheres can be subsequently bonded with CaP-prepared powder slurry or sol gel-modified slurries in the unfired state for producing aggregates. The aggregate form is created by sintering the agglomerates in a fabricated form. After sintering, aggregates are sized by well known ceramic granulating/grinding and sieving methods. An alternative bonding method comprises the use of CaP or calcium sulfate cement or other cement for bonding microspheres. One advantage of the aggregate method for fluidized bed applications is that the open pores of the bonded aggregate are used as sites for cell attachment and growth, thereby providing protection to the cultured cells and additional surface area for enhancing growth of cells. The starting sphere size can be used to control the open pore size and pore size distribution for optimizing cell growth of different cell types. The density of these microcarriers will, in general, be greater than 1.12 gms/cc in either individual microcarrier or aggregate form.

CaP Microspheres for Chromatographic Applications

The processing methods as set forth for CaP microsphere fabrication (e.g., CaP Microbead Processing Method for Producing a Suspendable Microcarrier Substrate and Alternate Method for Fabricating Hollow CaP Microcarriers with Diameters Less Than 500 Micrometers (Sol Gel Type System) described above) can be used to produce microspheres for use in chromatographic applications. In this application, a preferred embodiment for the microspheres is in the size range of about 10 to 100 micrometers diameter with open porosity in the range of about 20% to about 60% and a pore size range from about 0.01 to about 0.5 micrometers. Microsphere sizes larger than 100 micrometers, up to about 2 millimeters diameter in either the hollow or non-hollow sphere form, improve permeability by minimizing the resistance to flow in the chromatographic column while maintaining the ability to separate and purify proteins, enzymes, nucleic acids, viruses, and other macromolecules. In addition, the thin wall of the hollow porous microsphere improves permeability for greater efficiency of separation and purification.

Implantable CaP Microspheres and Aggregates of Bonded Microspheres

The processing methods as set forth for CaP microsphere fabrication (e.g., CaP Microbead Processing Method for Producing a Suspendable Microcarrier Substrate and Alternate Method for Fabricating Hollow CaP Microcarriers with Diameters Less Than 500 Micrometers (Sol Gel Type System) described above) also can be used to produce microspheres for use as a biomedical implant. In this application, a preferred embodiment for the microspheres is in the size range of about 500 micrometers to about 1,000 micrometers diameter. Compacts of microspheres in this size range produce an interstitial open porosity of about 60% with a pore size range of about 350 micrometers to about 500 micrometers. For other tissue in-growth applications, such as epithelial tissue, the microcarrier diameter size range can be adjusted to provide an open pore size range from about 50 micrometers to about 150 micrometers to facilitate tissue in-growth.

As stated previously, aggregates can be formed by bonding microspheres using the CaP slurry and cement methods (e.g., CaP Non-Suspendable Microcarrier with Open Porosity) and can be used for biomedical implant applications. Cemented aggregates offer the advantage of conformation to the implant site without subsequent sintering. In addition, these microspheres can be used with collagen to form a composite implantable material. The open pore size within the microsphere-bonded aggregates can be adjusted for specific tissue in-growth as stated above.

The microspheres and aggregates of microspheres discussed above can be used as carriers of biological growth factors and other pharmaceutical agents including anti-inflammatory and anti-tumor agents. Open porosity within the microsphere can be made by sintering at a temperature less than that required to fully densify the material, or by adding a pore former to the material. This open porosity can be adjusted to facilitate delivery of specific biological growth factors and pharmaceutical agents. The tissue growth factors or pharmaceutical agents are incorporated either as a coating on microspheres or aggregate, or are impregnated within the open porosity of the microsphere or aggregate. The size of the open porosity between individual microspheres and within aggregates of microspheres can be adjusted by changing the size of the microspheres. Also, these microspheres and aggregates can be used to culture tissues which may be subsequently implanted to augment tissue defects.

Hollow microspheres and hollow microspheres bonded in aggregates provide a central cavity as a reservoir for growth factors or other pharmaceutical agents. The hollow microsphere provides compressive strength due to its geometry as a basic sphere in distributing mechanical stress within its wall. In addition, the thin wall of the hollow microsphere can be replaced by tissue in-growth as the material within the wall resorbs. The degree of resorbability may be adjusted by changing the wall thickness, the amount and size of porosity within the wall, and the amount of HA, TCP, and/or other CaP phases. Generally, an increased amount of TCP increases the resorbability of the microsphere.

Aggregates of the material can be shaped by hand carving or mechanized grinding. The degree of carvability can be adjusted by changing the strength of the bond between the microspheres. This bond strength can be changed by adjusting the sintering temperature of the bonding slurry or by adjusting the bonding cement chemistry. As previously stated, aggregates formed with cements can also be molded and allowed to set and conform to the implant site, thereby reducing the need for grinding or carving to shape.

A typical application for microspheres and bonded aggregates of microspheres is the repair and augmentation of bony defects. Also, microspheres of smaller sizes can be used to augment soft tissue, e.g., cartilage defects.

An object of this invention is to provide appropriate forms of calcium phosphate ceramic materials to be fabricated in specific shapes and sizes for anchorage-dependent mammalian cell culturing applications. Fabricated forms of the calcium phosphate ceramic to be used as microcarriers in, for example, mammalian cell culture applications include hollow microspheres, solid spheres, aggregates of microspheres, multi-pore aggregates, polymeric and glass CaP composites. A variety of coatings that can be made highly porous or combined with organic or polymeric materials, including growth factors, to form composite structures also can be used in conjunction with these fabricated forms. Combinations of the aforementioned fabricated forms also can be used to make the microcarriers of the present invention. To achieve the objects of this invention, appropriate mixtures of hydroxylapatite, tricalcium phosphate, and/or other CaP compounds and, in certain cases, an open pore phase are used to enhance cellular growth through the higher surface area of the porous structure. Closed porosity is used to maintain buoyancy in growth media. Although more limited in application, calcium carbonate can be used in granular form, as a coating on a substrate carrier for cell culturing applications or as the Ca phase in polymeric composites. A major advantage of the CaP ceramic microcarriers is that the finished material can be heated to as high as 1,000° C. for decomposing organic cell culture components to recycle the microcarrier after its use in culture. This heating step can not be done with the polymeric/CaP composite microcarriers described herein. Other advantages of the CaP substrate as a microcarrier for cell culturing applications, as compared to polymeric materials, are that the CaP substrate is dimensionally stable, due to non-swelling, by absorption of media.

For bioreactor applications which require a suspendable form of microcarrier, the preferred form of the calcium phosphate substrate comprises a hollow microcarrier of about 0.2 to about 6 mm diameter that has been sintered to a sufficiently dense, impervious or impermeable state. For anchorage-dependent mammalian cells, the hollow microcarrier is suspended in the growth medium of the bioreactor. Therefore, a degree of buoyancy for the microcarrier is required. The preferred microcarrier density is in the range of about 1.00 to about 1.12 gms/cc. The density is more preferably in the range of about 1.00 to about 1.06 gms/cc. The hollow microspheres are fabricated from a CaP ceramic based on mixtures of HA and TCP, and/or other CaP compounds. The microsphere wall is of a controlled thickness in the unsintered state that varies depending on sphere size (see Table 1). The microsphere wall is sintered to a sufficiently dense state of about 3.0 gms/cc, or greater for HA/TCP mixtures to maintain an impervious state for suspendability. Alternatively, the open porosity structure can be sealed with a polymeric or other organic film former to achieve an impervious state.

U.S. Pat. No. 5,397,759 by Leonard Torobin teaches a process for fabricating porous ceramic hollow microspheres of uniform diameter and uniform wall thickness in sizes ranging from 1–4 mm in diameter. U.S. Pat. No. 5,225,123 by Leonard Torobin also teaches a process for fabricating hollow ceramic microspheres with closed porosity. The present invention uses aspects of this technology to produce a suspendable calcium phosphate ceramic for use in cell culture applications. An alternative technology for fabricating porous ceramic hollow spheres is described in U.S. Pat. No. 3,875,273 by Robert M. Martin. There also are other processes for fabricating hollow microspheres from ceramic materials as described by David Wilcox in *Hollow and Solid Spheres and Microspheres: Science and Technology Associated With Their Fabrication and Application*, Materials Research Society Symposium Proceedings, Volume 372, 1995. These fabrication methods include sacrificial cores, nozzle-reactor systems, emulsion/phase separation techniques (including sol gel processing), and mechanical attrition. Although these approaches do not specifically address calcium phosphate materials or cell culture microcarrier system applications, the described processes could be modified to produce the media suspendable calcium phosphate microcarrier systems of the present invention based on teachings herein. However, the aforementioned technologies must be combined with either commercial sources of calcium phosphate materials or be allied to the chemical formulation of hydroxylapatite and/or other calcium phosphate compounds such as tricalcium phosphate (tribasic calcium phosphate) in order to produce the carriers of the present invention. These materials are of primary interest, since they can be fabricated in dense non-permeable forms as taught by A. Tampieri in the *Journal of Material Science: Materials in Medicine*, Vol. 8, pp. 29–37, 1997.

The efficacy of cell culture microcarriers for anchorage-dependent cells can also be greatly improved by the use of coatings that enhance cell attachment. Cartwright and Shah in *Basic Cell Culture* (J. M Davis, supra.) indicate collagen, fibronectin, laminin, and Pronectin (synthetic fibronectin promoting better attachment) are coatings currently used to promote cell attachment. Cheung (Cheung, supra.) and others have also reported poly-lysine as a coating that promotes cell attachment and proliferation.

Other applications of hydroxylapatite bead materials (non-suspendable) for biotechnology include, for example, use for chromatographic filtration/separation columns as taught by Louis Lange in U.S. Pat. No. 5,492,822 for the isolation of human pancreatic cholesterol. The HA form of CaP is also used for the separation and purification of proteins, enzymes, nucleic acids, viruses, and other macromolecules. According to Bio-Rad in Bulletin No. 1115, HA has unique separation properties and high selectivity and resolution. Applications of HA chromatography include separation of monoclonal and polyclonal antibodies of different classes, antibodies which differ in light chain composition, antibody fragments, isozyme, supercoiled DNA from linear duplexes, and single-stranded from double-stranded DNA.

For biomedical implant applications, HA has been used in particulate, monolithic and coating forms for tissue augmentation, primarily bone. HA has a number of advantages as an implant material including biological attachment to bone tissue, outstanding biocompatibility, elastic modulus close to that of bone, other reasonable mechanical properties such as strength, and support of new bone growth.

HA also may be used as a host material for delivery of biological materials, including growth factors, and referred to herein as biological coatings, and other pharmaceutical agents including anti-inflammatory and anti-tumor agents. Hideki Aoki in *Medical Applications of Hydroxyapatite* discusses the properties and uses of HA for biomedical applications. U.S. Pat. No. 5,422,340 teaches the use of calcium phosphate particles as carriers for bone growth factors. For bone in-growth applications of HA, Kenna in U.S. Pat. No. 5,192,324 teaches that a particle size of +30 to −20 U.S. Standard mesh size provides pore sizes of 350 micrometers to 500 micrometers to facilitate bone in-growth.

Hydroxylapatite can be produced by a variety of methods including: 1) preparation from calcium nitrate and ammonium phosphate (E. Hayek and H. Newesely in *Inorganic Synthesis*, Jacob Kleinberg, editor, McGraw-Hill, New York, Vol. 7, pp 63–65, 1963, or S. Larsen et al in *Experimentia*, Vol. 27, No. 40, pp. 483–485, 1971, 2) synthesis from calcium hydroxide and phosphoric acid as described by J. Tagai et al in *Adv. Biomaterials* 2, pp 477–488, 1980, 3) sol gel processing as described by A. Deptula in the *Journal of Non Crystalline Solids* 2, pp. 477–488, 1980, and 4) hydrolysis of $CaHPO_4$ under heat and pressure (hydrothermal bomb) as described by A. Posner et al, *Acta Cryst.*, 11, p 308, 1958. Likewise, variations of these methods, well know in the art, are also used to produce hydroxylapatite.

Tricalcium phosphate can be produced by the partial decomposition of hydroxylapatite upon calcining at >1200° C. (A. Tampieri, supra.) and/or the reaction of a stoichiometric mixture of hydroxylapatite with $CaHPO_4$ with subsequent thermal processing at or above 900° C. as described by C. Rey (*Biomaterials* 11, p. 13 (1990).

EXAMPLE 1

Process for Producing CaP Hollow Microspheres for Mammalian Cell Culturing Applications CaP hollow ceramic spheres in the range of about 0.2 mm to about 6 mm in the unsintered state are produced from ceramic slurries using either a commercial source of starting CaP raw material (calcium phosphate tribasic) or a precipitated form of CaP based on the nitrate solution process as taught by Jacob Kleinberg, editor, *Inorganic Synthesis*, McGraw-Hill, New York, Vol. 7, pp. 63–65 (Hayek and Newesley), 1963. Using the commercial source of CaP raw material (FMC, Lawrence, Kans.) slurry processing properties are controlled by optimizing several variables, including slurry density-related to solids content, viscosity, particle size distribution, film stabilizing agents, and dispersing agents. The characteristic spheres are formed from slurries at around several thousand per minute. After forming the spherical geometry from the nozzle, the spheres are subsequently dried in free flight by loss of solvent with the aid of a high vapor pressure organic as the dispersing liquid. The dried spheres in the green state are polymer-bonded shells which are then conventionally fired to sinter the walls.

In more detail, the ceramic slurry is fed through the outer orifice of the nozzle, and the pressurized forming gas that produces the microsphere void is fed through a center orifice with the outer orifice acting as a metering area for size control. The basic coaxial nozzle process is set forth in U.S. Pat. Nos. 5,225,123 and 5,397,759 by Torobin. The forming gas, described above, acts as a blowing agent within the slurry droplet and expands during flight from the drop tower. This method of hollow microsphere formation is set forth in Wilcox, *Hollow and Solid Spheres and Microspheres: Science and Technology Associated With Their Fabrication and Application*, Materials Research Society Symposium Proceedings, Volume 372, 1995.

The advantage of the nozzle-reactor system is that it has been demonstrated, for a variety of ceramic materials, to meet exacting specifications on sphericity, size and wall thickness control. Well-designed nozzle systems dispense individual CaP slurry droplets, with precise control of dimensions, into a reactor for forming the microsphere geometry. In the reactor, the slurry droplet is converted to a firm hollow microsphere. The reactor in drop tower configuration is the preferred method for fabricating CaP hollow microspheres for use as suspendable microcarriers for anchorage-dependent cells grown in cultures.

Sintering of the fabricated hollow microspheres is conducted in the temperature range of about 1100° C. to 1350° C., for time periods of about 0.1 to 6 hours to density the outer wall of the microsphere to a sufficient level of impermeability to ensure the suspendability required in typical bioreactor applications using aqueous media. The product that results from this process comprises hollow microspheres with the preferred sphere densities of about 1.00 to about 1.06 gms./cc. For typical sphere diameters in the range of about 1 to 3 millimeters, sphere wall thicknesses must be controlled to size limits within the range of about 75 to about 250 micrometers to achieve sphere densities slightly greater than 1.00 gms/cc for optimizing suspendability. Table 1 sets forth the relationship of sphere density as a function of sphere wall thickness for typical 0.5 mm, 1 mm, 2 mm, and 3 mm diameter microspheres based on a typical calcium phosphate density of 3.0 gms./cc.

TABLE 1

CaP Sphere Diameter, Wall Thickness, Sphere Density Tables
Based on CaP Density of 3.0 Grams Per Cubic Centimeter

| Sphere Dia. (mm) | Wall Thk. (microns) | Sphere Density (gms/cc) |
| --- | --- | --- |
| 0.5 | 25 | 0.81 |
| 0.5 | 30 | 0.96 |
| 0.5 | 35 | 1.09 |
| 0.5 | 40 | 1.22 |
| 0.5 | 50 | 1.46 |
| 0.5 | 65 | 1.78 |
| 0.5 | 75 | 1.97 |
| 0.5 | 100 | 2.35 |
| 1.0 | 25 | 0.43 |
| 1.0 | 50 | 0.81 |
| 1.0 | 60 | 0.96 |
| 1.0 | 65 | 1.02 |
| 1.0 | 75 | 1.16 |
| 1.0 | 100 | 1.46 |
| 1.0 | 125 | 1.73 |
| 2.0 | 75 | 0.63 |
| 2.0 | 100 | 0.81 |
| 2.0 | 125 | 0.99 |
| 2.0 | 150 | 1.16 |
| 2.0 | 175 | 1.32 |
| 2.0 | 200 | 1.46 |
| 2.0 | 225 | 1.60 |
| 2.0 | 250 | 1.73 |
| 3.0 | 100 | 0.56 |
| 3.0 | 125 | 0.69 |
| 3.0 | 150 | 0.81 |
| 3.0 | 175 | 0.93 |
| 3.0 | 190 | 1.00 |
| 3.0 | 200 | 1.05 |
| 3.0 | 210 | 1.09 |
| 3.0 | 225 | 1.16 |
| 3.0 | 250 | 1.26 |

An alternative method for fabricating ceramic hollow spheres is set forth in U.S. Pat. No. 3,875,273 by Martin and can be used to manufacture the CaP microspheres of the present invention. However, it is not as readily scaled for high volume production needs. The Martin method produces porous ceramic microbeads which subsequently require sealing of the outer microsphere surface with a polymeric film to attain a suspendable microcarrier.

EXAMPLE 1A

Alternative Method for Producing CaP Hollow Microspheres with Diameters in the Size Range From 0.2 mm to 6.0 mm by Coating Wax or Other Organic Microbeads with CaP Compounds Hollow ceramic microspheres may also be fabricated by coating ceramic powders or slurries onto microbeads of wax or other organic materials and subsequently removing the wax microbead through thermal decomposition and/or solvent extraction. The resulting hollow ceramic microspheres are sintered to the desired density.

More specifically, a microbead of polyethylene wax or other wax or organic material is formed by spraying from a melt and re-solidifiing at a lower temperature. Size of the microbeads is determined by the size of the spraying orifice and the pressure under which the organic material or wax is sprayed. Wax or other organic microbeads also can be produced, for example, by compaction of wax powders by rolling in heated ball mills or pan pelletizers or by rolling the powders and gradually adding a solvent to the powders to consolidate them in the form of beads. The size of the beads is controlled by the particle size of the starting powder, heat of the ball mill or pan pelletizer, speed of rotation of the ball mill or pan pelletizer, size of the ball mill or pan pelletizer, length of rolling time, and amount and speed of addition of an organic solvent system. The desired size of bead is obtained by screening. This screening process also removes the unconsolidated powders from the powder consolidation method.

In the case of hollow ceramic (CaP) microspheres prepared from slurries, powders with a broad particle size distribution are prepared by ball milling dry powders. These powders are further reduced in particle size by wet milling. By this means, a slurry with a high solids content can be prepared as is well known in the art of preparation of ceramic powders and materials. Likewise, dispersants and binders can be milled with the slurry to produce a higher solids content, promote adherence to the wax/organic microbead and to promote stronger resulting ceramic microspheres. The solids content of slurry the controls the final density/porosity of fabricated ceramic microbead in the unsintered state. The prepared slurry is mixed with the previously described wax or organic microbeads of the desired size. The mixture is sprayed under pressure through an orifice of sufficient size to allow passage of the wax/organic beads with a coating of slurry. The slurry coating of the wax/organic microbeads may also be accomplished by converging the slurry mixture with a liquid mixture of the wax/organic microbeads such that the two streams of materials converge causing the coating of the ceramic slurry onto the wax/organic microbeads. The slurry-coated wax/organic microbeads are allowed to dry during falling in air or by drying in heated air sufficient to cause drying of the coating, but not melting or decomposing of the wax/organic microbead.

The coated microbeads are further classified to the desired sizes by screening through screens of the desired mesh sizes. The wax is removed from the ceramic-coated wax beads by heating the coated beads to melt and decompose the wax/organic substrate. The porosity of the unsintered ceramic-coated shell allows for the removal of the wax/organic substrate by melting and thermal decomposition. Likewise, the porosity of the unsintered ceramic-coated shell allows for removal of the wax/organic by solvent extraction or a combination of solvent extraction and/or thermal decomposition. After the fabricating step, the microspheres are further dried, sintered and classified to size and density by traditional sieving and air classification methods. The microspheres also may be classified to desired densities for buoyancy by liquid density separation methods.

In the case of preparation by compaction of ceramic powders onto wax/organic beads, wax/organic beads are prepared as previously described in this example. A fine ceramic powder distribution is obtained by numerous methods well known in the art. An example of such a method is dry ball milling and subsequent wet ball milling. The wet milled powder is subsequently dried and further ball milled or air jet milled to break up agglomerates. The resulting powder and wax/organic microbeads of the desired size are placed in a ball mill, pan pelletizer or other container and rolled or vibrated to compact the powders onto the wax/ organic microbead. The use of a dense micro-media may also be added to a ball mill or other container to further compact the powders onto the wax/organic microbeads. Furthermore, the resulting shell thickness and density of the ceramic coating is controlled by the energy imparted to the fabricated bead. The amount of energy is controlled by the amount of time of compaction, and speed of rotation or vibration, and/or addition of liquid to promote the agglomeration of powders onto the wax/organic microbeads. Excess or unconsolidated powders are removed from the coated microbeads by sieving through screens of sufficient size to retain the coated microbeads and allow excess powders and compacting media to pass through. The wax/organic is removed as previously described and the ceramic microspheres are classified to size by methods previously described in this example, and sintered to the desired density. The above-mentioned methods are applicable to the formation of CaP-coated wax/organic microbeads.

EXAMPLE 2

Method for Fabricating Hollow CaP Microcarriers with Diameters Less than 500 Micrometers (Modified Sol Gel Type System)

Using the method set forth by Hayek and Newesley in Jacob Kleinberg, editor, *Inorganic Synthesis*, McGraw-Hill, New York, Vol. 7, pp. 63–65, 1963 for the synthesis of hydroxylapatite, basic solutions of calcium nitrate and ammonium phosphate are prepared and adjusted to a pH above 9 to promote the precipitation of hydroxylapatite upon addition of the ammonium phosphate to the calcium nitrate. Upon completion of the reaction, the solids are allowed to partially settle and are then decanted from the reacting solution. The decanting process is then repeated three times with distilled $H_2O$. Care must be taken not to wash away the hydroxylapatite precipitate. Based upon initial reaction calculations, the precipitate is diluted to a solid concentration of approximately 15–20%. A dispersant such as Pluronic (BASF, Parsippany, NJ) may be titrated into this precipitate until a fluid "water-like" consistency is obtained. Using a method as set forth by Kyung Moh for non-CaP ceramics ("Sol Gel Derived Ceramic Bubbles", *Hollow and Solid Microspheres*, Material Research Society Proceedings, #372, ed. by D. L. Wilcox, 1995), a solids content consisting of 100 grams of CaP, 16 grams of acetone and 0.5 grams of methyl cellulose (Dow Chemical, Midland, Mich.) is added and stirred into an even consistency. The mix is covered with Parafilm wax (VWR Scientific, Chicago, Ill.) to prevent evaporation. This solution is subsequently sprayed into hot oleyl alcohol (at 95° C.). The nozzle size, pressure, and distance from the oleyl alcohol can be adjusted to give the desired microsphere size. The mixture of droplets and oleyl alcohol is stirred for approximately 20 minutes. The gelled bubbles are subsequently filtered from the oleyl alcohol and placed on a refractory dish or plate, dried at ~100° C. for 1 hour and fired at a rate of 100° C./hr to 1100–1300° C. for approximately 1 hour to obtain dense or semi-permeable hollow microspheres depending on the desired permeability. The microspheres can be separated into desired classifications by well known sieving, air classification methods, and/or buoyancy classification in solutions of desired densities.

EXAMPLE 3

Porous CaP Coatings for Bonding to the Substrate Surfaces of Hollow or Solid Beads or Microbead Materials Comprised of CaP, Glass, Other Oxide Ceramics, Polymers, Proteinaceous Materials or Composite Materials The surface of the hollow microsphere can also be altered by applying a porous layer of suitable particulate calcium phosphate ceramic which (1) will increase the chemical activity of the material due to the higher surface area of the material and (2) through larger interconnecting pore sizes, can also provide porous channels to accommodate cell and tissue in-growth.

The porous calcium phosphate coating composition is comprised of a commercial source of tricalcium phosphate powder (FMC, Lawrence, Kans.) which is either used as-received, or preferably, is calcined in the temperature range of 1100° C. to 1250° C. to slightly coarsen the material for making porous coatings. The tribasic calcium phosphate ceramic powder is readily processed in an aqueous medium or other solvent if desired. The aqueous vehicle can be used in a process that readily accommodates a dispersant for increasing solids while minimizing shrinkage during drying. It also accommodates an organic-based pore former that is the preferred method for generating porosity within the calcium phosphate structure after sintering. Typically, the pore former is added in sufficient quantity (>30 volume percent) to create a continuous porous phase when higher levels of porosity in the coating are desired. The aqueous tribasic calcium phosphate slurry is cast onto the surface of the microcarrier substrate and allowed to dry. The inclusion of a small amount (~1%) of an acrylic emulsion binder aids in providing higher green strength to the unfired microcarrier for improved handling, and offers resistance to cracking during the drying process.

For calcium phosphate hollow microspheres and other solid forms of calcium phosphate to ultimately be sintered to an impervious state, the preferred method for coating the microbead or other substrate surface is to pre-sinter the microbead to a temperature of about 1100–1300° C. This provides sufficiently high strength for slurry coating such that the coating and microcarrier can be co-sintered to bond the coating to the microcarrier substrate. The microcarrier substrate is densified during final sintering. Final sintering can be done at a higher temperature typically in the range of 1150–1400° C. This sinters the calcium phosphate microcarrier wall with the coating having residual porosity derived from the pore formers that are incorporated into the coating formulation. The resulting material is at least a two-layer calcium phosphate structure (the substrate is one of the layers) with a dense wall supporting a tailored porous coating layer for enhancing the chemical activity and in-growth potential for cells and tissues grown in culture. The amount and size of porosity can be altered based on changes in coating formulation. The amount and type of pore former is the primary material variable that controls the porous phase. Typically, the amount of porosity in the coating will be in the range of about 20–60% with the pore size controlled in either a fine distribution or coarser distribution, depending on the application. The fine pore size distribution is comprised of a majority of pores less than about 30 micrometers. The coarser pore size distribution will have pore channels in about the 30 to 80 micrometer range, but the pore size distribution can be further altered to produce an even coarser and/or finer pore size distribution for certain applications.

As an alternative to the slurry method of coating, a powder or particulate agglomerate of CaP may be directly bonded to the surface of the solid CaP, or other suitable substrate, using. a coating process that simulates a spray granulation (or disk pelletizing) processing method that is well known in the art as taught by J. Reed, *Principles of Ceramics Processing*, Second Edition, John Wiley & Sons, Inc. New York, 1995. Any form of the solid substrate, including a hollow CaP microsphere, is introduced in a contained system with a liquid or binder-liquid (such as an aqueous-based acrylic emulsion) and sprayed onto the surface to promote adhesion of the loose powder or particulate onto the solid substrate surface and subsequently sintered. The particulate may be an agglomerate of CaP powder that contains open porosity in order to increase surface area of the CaP material for greater activity in cell culturing applications.

A CaP coating, typical of the type described above, is not limited in application to the surface of hollow microspheres. Calcium phosphate coatings, as formulated and tailored to specific property needs, can also be applied to a variety of other substrate materials including, but not limited to, alumina, mullite, cordierite, or other ceramic materials all of which are examples of oxide materials. The porous coating can be applied to either a hollow or a solid microbead. The microbead is a substrate for bonding the porous calcium phosphate coating in an appropriate sintering cycle. In addition to the variety of oxide ceramic substrate materials that are available in either a hollow or solid microbead or both, other materials may be used in providing a substrate surface for bonding the porous calcium phosphate coating. Glass beads, with or without BioGlass (L. L. Hench, Univ. of Florida), as an example, offer the advantage of softening over a broad temperature range. The softening characteristic of glass is useful for bonding the calcium phosphate coating. Similarly, a polymeric substrate material, particularly one that has an amorphous phase in its structure, also may exhibit a softening effect with temperature or solvent treatment of the surface. This softening makes it easier to bond a calcium phosphate coating because of the softening and wetting of the particulate calcium phosphate coating material. Examples of polymeric/organic materials that have utility as a substrate in either a hollow or solid microsphere form include, but are not limited to, dextran, polyethylene, polypropylene, polystyrene, polyurethane, and collagen.

The porous structure of the calcium phosphate coating provides a large surface area interface that is well suited for culturing anchorage-dependent cells. In certain applications, growth enhancing materials, such as biological coatings, including growth factors which may be added separately in the porous structure or coated onto the surface of the coating, are useful in promoting cell and tissue growth with the calcium phosphate substrate providing additional mechanical and anchorage-dependent functionality. Collagen and other bio-adhesives (coated or added separately) provide special utility in promoting cell adhesion and are well suited for adapting to the coarse porosity in the CaP coating. Collagen also has the potential for forming "bridges" between individual CaP coated hollow or solid microbeads.

EXAMPLE 4

Porous Calcium Phosphate Coating for Application on Calcium Phosphate, Other Ceramic, Glass (BioGlass®), and Polymer Hollow Microspheres and Spheres A typical example of a porous calcium phosphate coating, having a fine pore size distribution, typically less than about 30 micrometers, is comprised of the following components:

|  | Volume Percent |
|---|---|
| As-received or Calcined Tribasic Calcium Phosphate Powder: | 50–80 |
| Com Starch Pore Former or Expancel 461-DE 20 | 20–50 |
| Total Calcium Phosphate and Fine Pore Former Components Aqueous Formulation: | 100 |
| Total Calcium Phosphate/Fine Pore Former Components | 25–40 |
| Distilled Water | 60–75 |
| Ammonium Polyacrylate Dispersant | 0.5–1.0 |

A typical example of a porous calcium phosphate coating having a coarse pore size distribution with the majority of pore sizes in the range of 30–60 micrometers is comprised of the following components:

|  | Volume Percent |
|---|---|
| As-received or Calcined Tribasic Calcium Phosphate Powder | 50–80 |
| Potato Starch Pore Former or Expancel 091 DE 80 | 20–50 |
| Total Calcium Phosphate and Coarse Pore Former Components Aqueous Formulation: | 100 |
| Total Calcium Phosphate/Coarse Pore Former Components | 25–40 |
| Distilled Water | 60–75 |
| Ammonium Polyacrylate Dispersant | 0.5–1.0 |

Material Sources:
  Tribasic Calcium Phosphate: FMC, Lawrence, Kans.
  Corn Starch: Argo Brand, CPC Int., Inc., Englewood Cliffs, N.J.
  Expancel Polymers: Expancel, Inc., Duluth, Ga.
  Potato Starch: Western Polymer Corp., Moses Lake, Wash.
  Polyacrylate Dispersant (Duramax D-3021): Rohm & Haas, Montgomeryville, Pa.

To reduce the surface area of the as-received tribasic calcium phosphate powder for ease of slurry processing at higher solids content, the material is calcined in the 1100–1250° C. temperature range prior to mixing with the pore former, water and dispersant components. The preceding porous coating formulations are sintered in the temperature range of about 1000° C. to 1300° C. for bonding to the surface of CaP or other ceramic spheres. For glass or polymer spheres, the coatings are bonded to the surface at a temperature near the softening point of the glass or polymer composition.

EXAMPLE 5

Aggregate Suspendable Microcarriers with Open Porosity

Microcarrier spheres are prepared as set forth above by the modified sol gel, the Torobin spray nozzle method or other methods adapted from procedures as set forth in *Hollow and Solid Microspheres* (D. Wilcox, supra.) The density of the hollow microspheres is adjusted to less than 1.0 gms/cc to offset the additional fired weight of the bonding CaP medium to be added. A slurry of CaP, made either from commercially available powders such as FMC (Lawrence, Kans.) or sol-prepared reacted sources (see Hayek and Newesley in Jacob Kleinberg, supra.) is prepared in $H_2O$ with a solids content of 15–35% by weight. Approximately 1% of methylcellulose (Dow Chemical, Midland, Mich.) and 6 drops of Pluronic (BASF, Parsippany, N.J.) per 20 gms of CaP solids is added to improve processing and green strength of formed aggregates. The slurry and microspheres are mixed together in a container until the slurry covers the microspheres with a thin coating. The coated spheres are subsequently placed in a form for containment during sintering. The form used for containment can either be thermally decomposed (paper container) during sintering or separated from the aggregate after sintering in a ceramic crucible. The green aggregate is dried at 100° C. for one hour and subsequently fired at a rate of about 100° C./hr to 1100–1300° C. for 1 hour to obtain composites of spheres with interconnecting open porosity. The fired aggregate can subsequently be pulverized, sieved and classified by liquid gravity separation into the desired size/density of aggregate which would allow for the growth of cells, during cell culture, within protected open pores, in addition to the outer surface of the aggregates.

EXAMPLE 6

Aggregate Suspendable Microcarriers with Closed Porosity

For a Cap hollow microsphere, the amount of enclosed porosity required to achieve suspendability is the range of about 60% to 70%. For other than a hollow microsphere, this amount of porosity is redistributed in an aggregate form having multiple enclosed pores. Microcarriers are fabricated by addition of foaming agents to CaP slurries, and subsequently drying these slurries, such that the enclosed bubbles formed during foaming remain in place to provide a closed multi-pore structure. A typical foaming agent is an organic wetting agent which in a slurry, exhibits low surface tension and is capable of creating a foamed structure with the mechanical shear of the slurry. Such foaming agents include, for example, a Triton X-100 surfactant (Spectrum Chemical Mfg. Corp., Gardena, Calif.). Another example of a foamed microcarrier is one created by a chemical reaction which produces gas that coalesces as bubbles within the CaP slurry (e.g., oxidation of hydrogen peroxide) and is subsequently dried and thermally processed.

In both cases, the foamed aggregates are sintered to approximately 1200 to 1350° C. such that interstitial CaP material between the voids is impermeable to liquid media penetration. These aggregates are made to have neutral buoyancy in liquid media by adjusting the CaP solids to void content of the monolith. These materials are subsequently ground by standard granulation techniques and classified by screening or air classification to the desired size needed in cell culture.

EXAMPLE 7

Composite Suspendable or Non-Suspendable Microcarriers

In forming suspendable composites, the amount of CaP filler additive that can be used relative to a polymer or glass material is directly related to the density of the bulk polymeror glass material. However, the solid form polymer or glass can be made to contain a significant amount of closed porosity phase to reduce its bulk density. For polystyrene or dextran as examples of polymers exhibiting utility as a cell culture material, the presence of closed porosity created by a foaming agent which lowers the bulk density, will allow for the addition of more CaP filler in meeting the suspendability requirement due to its higher density.

A glass or polymer hollow microsphere is the preferred composite pre-cursor. A composite structure is formed using CaP powder or particulate as filler material. The final desired density, for achieving buoyancy as a suspendable microcarrier, will take into account the polymer or glass phase, CaP filler phase and a substantial pore phase that results from the hollow microsphere-forming process. Process methods for forming hollow microsphere diameters in the size range of about 100 micrometers to about 6 millimeters are useful in this invention. A method that allows for a substantial void (e.g., about 30% to about 60% of the overall bulk volume) in the microcarrier provides the means for a high loading of CaP filler in forming the composite structure. Polymeric materials that can be used include polystyrene, dextran, polyethylene, and others available in hollow microsphere form. The example below illustrates the degree of CaP loading for such a polymeric hollow microsphere. Although higher in density, a hollow glass microsphere is also capable of accepting CaP filler loading for achieving suspendability.

EXAMPLE 8

CaP Filler Loading in Hollow Polymeric Microsphere

For a polymer with a 1.1 gms/cc density in a hollow microsphere form with 60% void volume, the bulk density is 0.44 gms/cc. Therefore, the following equation can be written:

$$x(0.44 \text{ gms/cc}) + (1-x)(3.0 \text{ gms/cc}) = 1.05 \text{ gms/cc as example of density for buoyancy for the composite}$$

where x=volume fraction of polymer in hollow microsphere form 1−x=volume fraction of CaP filler in the composite with x=0.76 as the volume fraction of hollow polymer microsphere, the corresponding volume fraction of CaP filler is 0.24 or 24%.

Non-suspendable composites of CaP can be prepared by the addition of CaP powders and/or particulates to conventional materials used in cell culture, such as polystyrene, collagen, dextran, gelatin, or glass as examples. Similar materials such as polyethylene, polyurethane, and silicones or the like could also be used. In the case of thermoplastic polymers, sufficient CaP could be added to the melted polymer to bond the powders or particulates into a coherent mass of sufficient strength to resist crumbling during cell culture. CaP particle loading ranges can be from about 10 to 80 volume per cent and are adjustable to the requirements of the culture of specific cells. Likewise, the CaP powders/particulates can be added to liquid/collagen or gelatin slurries in equivalent previously cited ranges of CaP volume per cent sufficient to maintain mechanical integrity in cell culture environments. In the aforementioned cases, the materials can be either dried under heat or frozen and subsequently broken up by standard means of granulation to the desired particle sizes, or atomized by spray drying or other conventional polymer processing techniques, as previously described, and further classified by standard sieving methods. A similar process could also be used in the case of CaP additions to glass, although the CaP material would have to be added to the melted glass preferably below 1300° C. The melted glass is subsequently cooled to room temperature and ground/classified to size or atomized from the melt to produce particulates, which are classified to the desired sizes. All of these composites could be used as cell culture substrates or in discrete particulate forms in cell culture-packed beds or fluidized beds that require higher density as previously described. Likewise, the activity of the CaP filler can be further enhanced by abrading the surface of the composite structures.

EXAMPLE 9

CaP Non-Suspendable Microcarrier with Open Porosity

CaP ceramic microspheres in the range of about 0.5 mm to about 6 mm in the unsintered state are produced from ceramic slurries using either a commercial source of starting CaP raw material (calcium phosphate tribasic) or a precipitated form of CaP based on the nitrate solution process as taught by Jacob Kleinberg, editor, *Inorganic Synthesis*, McGraw-Hill, New York, Vol. 7, pp. 63–65 (Hayek and Newesley), 1963. Using the commercial source of CaP raw material (FMC, Lawrence, Kans.), slurry processing properties are controlled by optimizing several variables, including slurry density-related to solids content, viscosity, particle size distribution, organic binders, including pore formers, and dispersing agents. Slurry processing is followed by spray drying which is performed using conventional methods well known in the art as taught by K. Masters, *Spray Drying*, Leonard Hill Books, London, England, 1972. The preferred method for producing microspheres with diameters greater than one (1) millimeter is by disk pelletizing which is well known in the art of ceramic processing. Methods for producing open porosity include the previously cited organic pore formers, and/or by sintering the microspheres to a temperature less than that required to completely density the material, e.g., about 1100° C. for the HA form of CaP. The coaxial nozzle process as set forth in Example 1 above can also be used to produced hollow microspheres with open porosity. Open porosity is obtained by lower temperature sintering as described above. An alternative method for fabricating ceramic hollow spheres is set forth in U.S. Pat. No. 3,875,273 by Martin and can be used to manufacture the CaP microspheres of the present invention.

EXAMPLE 10

Aggregate CaP Non-Suspendable Microcarrier with Open Porosity

Microcarrier spheres are prepared as set forth above in Example 9. A slurry of CaP, made either from commercially available powders such as from FMC (Lawrence, Kans.) or sol-prepared reacted sources (see Hayek and Newesley in Jacob Kleinberg, supra.), is prepared in $H_2O$ with a solids content of about 10–20% by weight. Approximately 1% of methylcellulose (Dow Chemical, Midland, Mich.) and 6 drops of Pluronic (BASF, Parsippany, N.J.) per 20 gms of CaP solids is added to improve processing and green strength of formed aggregates. The slurry and microspheres are mixed together in a container until the slurry covers the microspheres with a thin coating. The coated spheres are subsequently placed in a form for containment during sintering. The form used for containment can either be thermally decomposed during sintering or separated from the aggregate after sintering. The green aggregate is dried at 100° C. for one hour and subsequently fired at a rate of about 100° C./hr to about 1100° C./hr to obtain bonded microspheres with interconnecting open porosity. An alternative method for bonding microspheres to make aggregates uses a CaP cement as taught by L. Chow and S. Takagi in U.S. Pat. No. 5,525,148. The fired or cement-bonded aggregate can subsequently be pulverized, sieved and classified by liquid gravity separation into the desired size/density of aggregate which would allow for the growth of cells, during cell culture, within protected open pores, in addition to the outer surface of the aggregates.

For Examples 1–10, the CaP microcarriers can be used in conventional cell culturing systems. For example, in cell cultures comprising the BHK 21 (baby hamster kidney) cell line, BHK 21 cells are anchored to the surface of the CaP microcarrier. This cell line may be used to produce IL2 (Interleukin 2 Factor) by secretion (Carwright, supra).

EXAMPLE 11

CaP Microspheres for Chromatographic Applications

Microspheres for this application are produced by the processing methods set forth in Examples 1, 1A, and 2 with the exception that the microspheres are sintered to less than fill density to make open interconnected porosity in the range of about 20% to 50% and a pore size range from about 0.01 to 0.5 micrometers. This open porosity is produced by sintering the microspheres at a temperature in the range of about 1100° C. to 1200° C. An example of an application is the separation of single-and double-stranded DNA in a HA column as taught by K. Sundaram and L. Loane, "Liquid Chromatographic Assay For The Separation of Single- and Double-Stranded DNA By Using UV and UV Diode-Array Detectors and Hydroxylapatite Column", *Journal of Liquid Chromatography*, 18(5), 925–939 (1995).

EXAMPLE 12

Implantable CaP Hollow Microspheres

Hollow microspheres with a diameter of about 500 micrometers are produced by methods set forth in Examples 1, 1A, and 2 with the exception that the microspheres are sintered to less than full density to make open interconnected porosity in the range of about 20% to 30% and a pore size range from about 0.1 to 1.0 micrometers. These microspheres are placed in a solution containing transforming growth factor—beta to infiltrate and coat the microspheres with the growth factor for the repair of bone defects as taught by A. Ammann et al. in U.S. Pat. 5,422,340. The amount of growth factor in the microsphere can be increased by infiltrating under vacuum. The microspheres are suspended in saline in a syringe and subsequently delivered to the bone defect site. An alternative method for delivering the microspheres for implantation is to mix the microspheres with CaP cement at the time of implantation. The cement as taught by L. Chow and S. Takagi in U.S. Pat. No. 5,525,148 can be used for this method.

EXAMPLE 13

Implantable CaP Aggregate with Bonded Hollow Microspheres

An aggregate for this application is produced by methods set forth in Example 10 with the exception that the aggregate is left in a monolithic form and is not ground or pulverized.

The aggregate is subsequently infiltrated with the transforming growth factor—beta as described in Example 12. During implantation, the monolith is carved to the desired implant shape and inserted in the defect site.

The foregoing description of the invention is only exemplary for purposes of illustration. Without departing from the spirit and scope of the invention, one skilled in the art can make changes and modifications to the invention to adapt it to various uses and conditions. Such changes and modifications are within the scope of the disclosed invention.

All documents referred to herein are incorporated by reference.

DOCUMENTS

1. A. O. Miller, F. D. Menozzi, and D. Dubois, "Microbeads and Anchorage-Dependent Eukaryotic Cells: The Beginning of a New Era in Biotechnology", *Advances in Biochemical Engineering Biotechnolog,* 39, 73–95, 1989.
2. M. W. Glacken, R. J. Fleishaker, and A. J. Sinskey, "Mammalian Cells in Culture. Engineering Principles and Scale-up, *Trends in Biotechnoloay,* 1, 102–108, 1983.
3. H. S. Cheung, M. T. Stony, and D. J. McCarty, "Mitogenic Effects of Hydroxylapatite and Calcium Pyrophosphate Dihydrate Crystals on Cultured Mammalian Cells", *Arthritis Rheum,* 27, 688–674, 1984.
4. H. S. Cheung and D. J. McCarty, "Calcium Containing Crystals Can Substitute for Platelet Derived Growth Factor (PDGF) in Cell Culture, *Arthritis Rheum,* 26, S60 (Abstract Only), 1983.
5. H. S. Cheung et al, "Phagocytosis of Hydroxylapatite or Calcium Pyrophosphate Dihydrate Crystals by Rabbit Articular Chondrocytes" *Proceedings of the Society for Experimental Biology and Medicine,* 173, 181–189, 1983.
6. H. S. Cheung, U.S. Pat. No. 4,757,017, In Vitro Cell Culture System, Jul. 12, 1988.
7. G. Guillemin et al, U.S. Pat. No. 5,480,827, Use Of Porous Polycrystalline Aragonite As A Support Material For In Vitro Culture of Cells, Jan. 2, 1996.
8. Anthony S. Lubiniecki, *Large Scale Mammalian Cell Culture Technology*, Marcel Dekker, Inc., New York, pp 286–287, 1990.
9. T. M. Henderson, U.S. Pat. No. 4,448,884, Glass Surface Microcarrier For Growth Of Cell Cultures, May 15, 1984.
10. Gregory Stephanopoulos, U.S. Pat. No. 5,262,320, Cell-culturing Apparatus and Method Employing a Macroporous Support, Nov. 16, 1993.
11. Walter Trosch et al., U. S. Pat. 4,987,068, Porous Inorganic Support Spheres Which Can Be Cleaned of Surface Biomass Under Fluidized Bed Conditions, Jan. 22, 1991.
12. Richard Peindl, U.S. Pat. No. 5,538,887, Cell Culture Apparatus Having Smooth Surface for Cell Growth Thereon, Jul. 23, 1996.
13. Louis Lange, U.S. Pat. No. 5,492822, Method for Recovering 100,000 Dalton Molecular Weight Fraction Of Human Pancreatic Cholesterol Esterase. Feb. 20, 1996.
14. Leonard B. Torobin, U.S. Pat. No. 5, 397,759, Hollow Porous Microspheres Made From Dispersed Particle Compositions, Mar. 14, 1995.
15. Leonard B. Torobin, U.S. Pat. No. 5,225,123, Methods for Producing Hollow Microspheres Made from Dispersed Particle Compositions, Jul. 6, 1993.
16. Robert M. Martin, U.S. Pat. No. 3,875,273, Hollow Pellets and Method of Making Same, Apr. 1, 1975.
17. David L. Wilcox, *Hollow and Solid Spheres and Microsoheres: Science and Technology Associated With Their Fabrication and Application*, Materials Research Society Symposium Proceedings, Volume 372, 1995.
18. Jacob Kleinberg, editor, *Inorganic Synthesis*, McGraw-Hill, New York, Vol. 7, pp 63–65 (Hayek and Newesley), 1963.
19. S. Larsen et al *Experimentia,* Vol. 27, No. 40, pp 483–485, 1971.
20. J. Tagai and H. Aoki, *Adv. Biomater.* 2, pp. 477–488, 1980.
21. A. Deptula et al, *Journal of Non-Crystalline Solids,* 147–148, pp. 537–541. 1992.
22. A. S. Posner et al, *Acta Cryst.,* 11, p 308, 1958.
21. A. Tampieri, et al, *Journal of Material Science: Materials in Medicine,* Vol 8, pp 29–37, 1997.
22. J. M. Davis (editor), *Basic Cell Culture*, (Cartwright and Shah), Oxford University Press, New York, 1994.
23. Ian Freshney, *Culture of Animal Cells. A Manual of Basic Technique.* 2nd Ed., Alan R. Liss, Inc., New York, 1987.
24. E. Adema, D. Shnek, F. Cahn, and A. J. Sinskey, "Use of Porous Microcarriers in Agitated Cultures", Biopharm, V.3, No. 7, Jul.–Aug., 20–21, 23, 1990.
25. A. L. Smiley, W- S. Hu, and D. I. C. Wang, "Production of Human Immune Interferon by Recombinant Mammalian Cells Cultivated on Microcarriers", *Biotechnology and Bioengineering,* 33, 1182–1190, 1989.
26. F. Cahn, "Biomaterials Aspects of Porous Microcarriers for Animal Cell Culture", TIBTECH, 8, May 1990.
27. James S. Reed, *Principles of Ceramic Processing*, Second Edition, John Wiley and Sons, New York, pp. 215–228, 1995.
28. D. Looby and J. Griffiths, "Immobilization of Cells In Porous carrier culture", *Trends Biotechnology,* 8: 204–209, 1990.
29. S. Park and G. Stephanopoulos, "Packed Bed Reactor with Porous Ceramic Beads for Animal Cell Culture, *Biotechnology Bioengineering,* 41: 25–34, 1993.
30. D. W. Lee et al, "High Intensity Growth of Adherent Cells On a Porous Ceramic Matrix. *Production of Biologicals from Animal Cells in Culture*, editors, R. E. et al, Butterworth-Heinemann pp. 400–405, 1991.
31. T. Cartwright, *Animal Cells as Bioreactors*, Cambridge University Press, New York, pp. 78, 1994.
32. T. Matsushita et al, "High Density Culture of Anchorage Dependent Animal Cells by Polyurethane Foam Packed Bed Culture Systems", *Applied Microbiology Biotechnology,* 35: 159–64, 1991.
33. C. Rey, *Biomaterials* 11, p. 13 (1990).
34. Bio-Rad, "Bio-Gel® HPHT for Protein and Nucleic Acid HPLC: New High Performance Hydroxylapatite Column in Bulletin No. 1115, Bio-Rad Labs, 1414 Harbour Way South, Richmond, Calif. 94804, 1996.
35. Masters, *Spray Dryig*, Leonard Hill Books, London, England, 1972.
36. Sundaram and L. Loane, "Liquid Chromatographic Assay For The Separation of Single- and Double-Stranded DNA By Using UV and UV Diode-Array Detectors and Hydroxylapatite Column", *Journal of Liquid Chromatogaphy,* 18(5), 925–939 (1995).
37. L. Chow and S. Takagi, U.S. Pat. No. 5,525,148, Self-setting Calcium Phosphate Cements and Methods for Preparing and Using Them, Jun. 11, 1996.
38. H. Aoki, *Medical Applications of Hydroxyapatite*, Isiyaku EuroAmerica, Inc., Tokyo, Japan, 1994
39. A. Ammann et al., U.S. Pat. No. 5,422,340, TGF-beta Formulation for Inducing Bone Growth, Jun. 6, 1995
40. R. Kenna, U.S. Pat. No. 5,192,324, Bone Prosthesis with Porous Coating, Mar. 9, 1993.

We claim:

1. A biomedical implant comprising a hollow microbead of a calcium phosphate material, wherein the microbead has a density from about 25% to about 75% of the material's theoretical density.

2. A biomedical implant, as claimed in claimed in claim 1, further comprising a compound seated from the group consisting of a biological coating and a pharmaceutical agent.

3. A biomedical implant, as claimed in claim 1, wherein the microbead comprises a wall which is essentially impermeable to aqueous media.

4. A biomedical implant, as claimed in claim 1, wherein the microbead comprises a wall which is porous.

5. A biomedical implant, as claimed in claim 1, wherein the microbead comprises at least one hole.

6. A biomedical implant comprising an aggregate of hollow calcium phosphate microbeads, as claimed in claim 1, wherein the microbeads have a density from about 1.0 grams/cc to about 2.0 grams/cc.

7. A chromatographic column comprising an aggregate of hollow microbeads of a calcium phosphate material wherein the microbeads have a density from about 25% to about 75% of the material's theoretical density.

8. A microbead, wherein said microbead:
   is selected from the group consisting of hollow microbeads and solid microbeads;
   is selected from the group consisting of glass microbeads and polymer microbeads; and
   is formed with or coated with a particulate calcium phosphate.

9. A microbead, as claimed in claim 8, wherein the surface of said microbead abraded.

10. An aggregate of microbeads, as claimed in claim 8.

11. An aggregate, as claimed in claim 10, further comprising a coating selected from the group consisting of HA coatings, TCP coatings, porous coatings, biological coatings, and pharmaceutical agents.

12. A biomedical implant comprising the aggregate of claim 11.

13. A biomedical implant, as claimed in claim 12, wherein said aggregate is bonded by cementations agents.

14. A chromatographic column comprising the aggregate according to claim 10.

15. A microbead, wherein said microbead is selected from the group consisting of hollow microbeads and solid microbeads, and wherein said microbead is a composite of (i) a calcium phosphate and (ii) a material selected from the group consisting of a ceramic material and a polymeric material.

16. A microbead, as claimed in claim 15, wherein the surface of said microbead is abraded.

17. An aggregate of microbeads, as claimed in claim 15.

18. An aggregate, as claimed in claim 17, further comprising a coating selected from the group consisting of HA coatings, TCP coatings, porous coatings, biological coatings and pharmaceutical agents.

19. A biomedical implant comprising the aggregate of claim 18.

20. A biomedical implant, as claimed in claim 17, wherein said aggregate is bonded by cementatious agents.

21. A chromatographic column comprising the aggregate according to claim 17.

22. An aggregate comprising microbeads having foamed structures of a material selected from the group consisting of ceramic, glass, and polymeric materials and composites thereof; wherein said foamed structures are selected from the group consisting of closed pores, open pores and combinations of closed and open pores; and wherein said aggregate is selected from the group consisting of a suspendable aggregate and a non-suspendable aggregate.

23. A biomedical implant comprising the aggregate of claim 22.

24. A biomedical implant, as claimed in claim 23, further comprising biological coating.

25. A biomedical implant, as claimed in claim 23, wherein the microbead has a density from about 25% to about 75% of the material's theoretical density.

26. An aggregate, as claimed in claim 22, further comprising a coating selected from the group consisting of HA coatings, TCP coatings, porous coatings, biological coatings and pharmaceutical agents.

27. A biomedical implant comprising the aggregate of claim 26.

28. A biomedical implant, as claimed in claim 27, further comprising a biological coating.

29. A biomedical implant, as claimed in claim 27, wherein the microbead has a density from about 25% to about 75% of the material's theoretical density.

30. A chromatographic column comprising the aggregate according to claim 22.

31. A biomedical implant, comprising an aggregate of hollow calcium phosphate (CaP) microbeads, wherein the microbeads have a density from about 1.0 grams/cc to about 2.0 grams/cc, wherein the microbeads are bonded by cementations agents.

32. A hollow calcium phosphate (CaP) microbead having a density from about 1.00 grams/cc to about 2.00 grams/cc and comprising a compound selected from the group consisting of a biological coating and a pharmaceutical agent.

* * * * *